US008285246B2

(12) United States Patent
Doerr

(10) Patent No.: US 8,285,246 B2
(45) Date of Patent: Oct. 9, 2012

(54) IMPLANTABLE MEDICAL DEVICE AND MOBILE WIRELESS MODEM

(75) Inventor: Thomas Doerr, Berlin (DE)

(73) Assignee: BIOTRONIK CRM Patent AG (CH)

( * ) Notice: Subject to any disclaimer, the term of this patent is extended or adjusted under 35 U.S.C. 154(b) by 341 days.

(21) Appl. No.: 12/627,101

(22) Filed: Nov. 30, 2009

(65) Prior Publication Data

US 2010/0152550 A1 Jun. 17, 2010

(30) Foreign Application Priority Data

Dec. 15, 2008 (DE) .......................... 10 2008 054 658

(51) Int. Cl.
| | |
|---|---|
| *H04M 11/04* | (2006.01) |
| *H04M 1/00* | (2006.01) |
| *H04B 17/00* | (2006.01) |
| *H04B 1/04* | (2006.01) |
| *H04B 7/00* | (2006.01) |
| *H01Q 11/12* | (2006.01) |
| *H04W 4/00* | (2009.01) |
| *A61B 19/00* | (2006.01) |
| *A61B 5/04* | (2006.01) |
| *A61N 1/00* | (2006.01) |
| *A61K 9/22* | (2006.01) |

(52) U.S. Cl. ................ 455/404.1; 455/67.11; 455/127.5; 455/434; 455/512; 455/513; 455/556.1; 128/899; 128/903; 600/377; 607/60; 604/891.1

(58) Field of Classification Search ................... 128/899; 128/903; 379/48; 455/67.11, 127.5, 404.1, 455/434, 556.1; 600/301; 607/60

See application file for complete search history.

(56) References Cited

U.S. PATENT DOCUMENTS 6,078,816 A * 6/2000 Weiss et al. ................... 455/450

(Continued)

FOREIGN PATENT DOCUMENTS

DE 102 02 448 A1 8/2003

(Continued)

OTHER PUBLICATIONS

Schmidt, Craig L, et al. "The future of lithium and lithium-ion batteries in implantable medical devices", Journal of Power Sources 97-98 (2001), pp. 742-746.*

(Continued)

*Primary Examiner* — Ariel Balaoing
*Assistant Examiner* — Larry Sternbane
(74) *Attorney, Agent, or Firm* — Craig A. Fieschko, Esq.; DeWitt Ross & Stevens S.C.

(57) ABSTRACT

An electronic implant is designed to detect at least one technical or physiological patient parameter, and has an exhaustible power source. The electronic implant also has an integrated mobile wireless antenna, a low-current mobile wireless modem with a low maximum transmission power, a low-current mobile wireless field-strength-measuring unit, and a control unit connected to the field-strength-measuring unit and to the mobile wireless modem. The control unit triggers access to a mobile wireless network as a function of the transmission power needed for data transmission by the low-current mobile wireless modem, taking into account a mobile wireless field strength value determined by the field-strength-measuring unit, and also taking into account the urgency of the data content to be transmitted. Network access only occurs when the needed transmission power does not exceed a specific maximum value for the particular urgency.

18 Claims, 6 Drawing Sheets

U.S. PATENT DOCUMENTS

| | | | |
|---|---|---|---|
| 6,497,655 B1 | 12/2002 | Linberg et al. | |
| 6,718,171 B1 | 4/2004 | Hunzinger | |
| 7,489,652 B2* | 2/2009 | Kwon et al. | 370/328 |
| 7,793,316 B2* | 9/2010 | Mears et al. | 725/9 |
| 7,948,362 B2* | 5/2011 | Bungartz et al. | 340/10.33 |
| 2001/0023360 A1 | 9/2001 | Nelson et al. | |
| 2001/0031997 A1 | 10/2001 | Lee | |
| 2001/0037220 A1 | 11/2001 | Merry et al. | |
| 2001/0039375 A1 | 11/2001 | Lee et al. | |
| 2002/0123673 A1 | 9/2002 | Webb et al. | |
| 2003/0041866 A1 | 3/2003 | Linberg et al. | |
| 2004/0122489 A1* | 6/2004 | Mazar et al. | 607/60 |
| 2007/0032832 A1 | 2/2007 | Feher | |
| 2007/0258395 A1* | 11/2007 | Jollota et al. | 370/310 |
| 2009/0111390 A1* | 4/2009 | Sutton et al. | 455/77 |
| 2009/0248116 A1* | 10/2009 | Le Reverend et al. | 607/60 |
| 2009/0252042 A1* | 10/2009 | Bradley et al. | 370/241 |

FOREIGN PATENT DOCUMENTS

| | | |
|---|---|---|
| WO | WO 0234038 A | 5/2002 |
| WO | WO 03/095024 A2 | 11/2003 |

OTHER PUBLICATIONS

Saadaoui, S., Wolf, L., Architecture Concept of a Wireless Body Area Sensor Network for Health Monitoring of Elderly People. In: Consumer Communications and Networking Conference, 2007, ISBN 1-4244-0667-6, S.722-726 S.722,Sp.re., Abs. 1,S.723,SP.li.,Abs. 2,5,S.723, Sp.re., Abs.6,7,S.725,Sp.re., Abs.2.

* cited by examiner

IMPLANTABLE MEDICAL DEVICE AND MOBILE WIRELESS MODEM

FIELD OF THE INVENTION

The invention relates to a permanently implantable electronic implant which is designed to detect at least one technical or physiological parameter. The invention relates in particular to implantable pulse generators, such as cardiac pacemakers, cardioverter/defibrillators or the like.

BACKGROUND OF THE INVENTION

Remote monitoring of electronic implants, such as cardiac pacemakers, implantable defibrillators, or neurostimulators is becoming increasingly important. These implants transmit data at regular intervals (e.g., once a day) or by event-triggered transmission to a remote monitoring server to which the physician has access via a data link, and thus can perform remote monitoring.

All currently known approaches must rely on a relay station (e.g., BIOTRONIK Cardio Messenger) for transmission of data from the electronic implant to a data transmission network (mobile wireless network, telephone network, etc.). Data transmission from the electronic implant to the relay station via MICS band (in some cases also ISM band) is preferably used here.

The disadvantage of this approach is that the patient must carry an additional cost-intensive external accessory device within the range of the implant to ensure data transmission from the implant to the transmission network. These external accessory devices can be regarded as a weak point in this transmission link because they are often not operated correctly by the patient, or they are not within the range of the patient (patient compliance). In some cases, these devices encounter rejection by the patient and result in psychological side effects because the patient is constantly being reminded of the electronic implant (anxiety, control compulsion, etc.).

FIG. 1 shows the current state of the art. An electronic implant 110 has an MICS band transceiver and at periodic intervals sends signals representing values of technical and/or physiological parameters measured with the implant to a relay station 120, which must be located in the immediate vicinity of the patient bearing the electronic implant 110 at the time of the transmission. This relay station 120 then transmits the data sent by an integrated GSM modem to a GSM base station 130, which then transmits this data in turn over a mobile wireless network 140 to a remote monitoring server 150, and thus makes the data available to the physician 160.

The relay station 120, also called the patient device, may be implemented in a mobile or stationary version. A conventional telephone network link may be used for data transmission with a stationary patient device 120.

Reliable data transmission is usually possible only when the patient device 120 is activated and is situated a maximum distance of 2-5 meters from the electronic implant 110.

SUMMARY OF THE INVENTION

An object of the invention is to implement a data link for remote transmission of an electronic implant between the implant and a mobile wireless network (e.g., a GSM network) without an additional relay station. This object is at least partially achieved by a permanently implantable electronic implant which is designed to detect at least one technical or physiological parameter, and which has a exhaustible current source or voltage source, usually a battery. The electronic implant has a low-current mobile wireless modem having a low maximum transmission power, which is connected to a mobile wireless antenna integrated into the electronic implant. The statements "low current" (consumption) and "low maximum transmission power" serve to permit a better understanding of the relationship and refer to GSM modems, which are customary today for data transmission.

Furthermore, the implant has a low-current mobile wireless field-strength-measuring unit connected to the mobile wireless antenna or to a second antenna and has a control unit which is connected to the field-strength-measuring unit and to the mobile wireless modem.

The control unit is designed to trigger access to the mobile wireless network as a function of (1) a prevailing output value of the field-strength-measuring unit (i.e., a prevailing field strength value), and (2) the urgency of a data content to be transmitted, only when the prevailing output value of the field-strength-measuring unit indicates a specific minimum transmission success rate for a particular urgency.

In a simple case, this may mean (for example) that when the transmission power presumably required when a mobile wireless field strength value determined by the field-strength-measuring unit is taken into account, the control unit triggers access only when this field strength value does not exceed a maximum value assigned to a particular urgency.

The integration of a GSM modem into an electronic implant is assumed as known here (see: US 2007/0032832 A1), whereby the approach of depletability of the battery of a permanent electronic implant known from US 2007/0032832 A1 is not taken into account. Accordingly, the approach used by the invention allows a mobile wireless modem to be operated in an electronic implant at such a low current that its use is justified, when measured by the expected shortening of the operating time due to the data transmission.

The invention is based on the assumption that the user of an electronic implant will in the future always be within the range of mobile wireless cells, e.g., GSM cells, so that one or more times a day, above-average-quality transmission and reception conditions will also exist. These are to be utilized by the invention, and the connection to a mobile wireless base station is to be established only under these conditions.

For patients for whom this assumption is not correct, in the future presumably so-called Home-GSM cells will be offered by GSM manufacturers for operation in the domestic environment.

The mobile wireless modem is preferably a GSM modem and the mobile wireless field-strength-measuring unit is a GSM field-strength-measuring unit. The electronic implant preferably includes a subscriber identity module, e.g., in the form of a SIM card.

In a preferred version of the invention, the electronic implant also has a statistics unit which is connected to or is part of the control unit. The statistics unit is designed to record access success statistics of access attempts triggered as a function of a particular field strength value measured before a particular access attempt on the part of the mobile wireless field-strength-measuring unit. The control unit here may be designed to trigger access, also taking into account the access success statistics for a particular measured mobile wireless field strength value.

In addition, the statistics unit may record the access success statistics, taking into account the particular point in time of access, and the control unit can determine the point in time of the next access time window and/or field-strength-measuring window on the basis of the access success statistics. The incidence of successful connections established with recurring ambient conditions (e.g., good GSM reception at the workplace) can be increased. The energy consumption for determination of the transmission conditions can also be reduced by such a field strength measurement.

In particular the control unit may determine the particular maximum value for the required transmission power by analyzing the access success statistics as a function of the urgency of the particular data content to be transmitted, so that (for example) an emergency case report can be transmitted even under inferior transmission conditions, whereas a less relevant message is transmitted only under very favorable transmission conditions.

In another preferred version of the invention, the electronic implant has two current sources or voltage sources, one of which is intended for supplying power to a mobile wireless unit independently of other units of the electronic implant and is designed as a rechargeable battery (preferably wirelessly and transcutaneously rechargeable). The mobile wireless unit in this version preferably includes at least the mobile wireless modem and may additionally include the mobile wireless field-strength-measuring unit, for example.

In addition to the mobile wireless field-strength-measuring unit, the electronic implant preferably has a very nonspecific GSM field-strength detector, which is designed to activate the mobile wireless field-strength-measuring unit either directly or by means of the control unit only when the very nonspecific GSM field-strength detector indicates a minimum field strength (threshold value). The electronic implant may therefore have an amplifier, a comparator for threshold value comparison and a trigger unit for activation of the field-strength-measuring unit when the threshold value is exceeded.

The control unit is preferably designed to trigger at most one access attempt within an adjustable period of time, e.g., one day.

Furthermore, the control unit may be designed to limit the number of access attempts within a particular period of time, such that only a predetermined maximum percentage (e.g., 25%) of the capacity of the exhaustible current source or voltage source is used for transmission of data via the mobile wireless modem. The control unit here may be designed to trigger access in the event of data content containing an emergency message, regardless of the capacity of the exhaustible current source or voltage source.

In addition, the control unit may be designed to trigger access to a mobile wireless network only for data content generated by a technical or physiological event detected by the electronic implant. For example, these may be emergency messages, which are triggered by detection of health states that are to be considered dangerous.

The control unit may also be designed to trigger access via an emergency telephone number only in the event of data contents containing emergency messages.

BRIEF DESCRIPTION OF THE DRAWINGS

The invention will now be explained in greater detail on the basis of an exemplary version with reference to the figures. Of these.

DETAILED DESCRIPTION OF THE INVENTION

Figure 1:
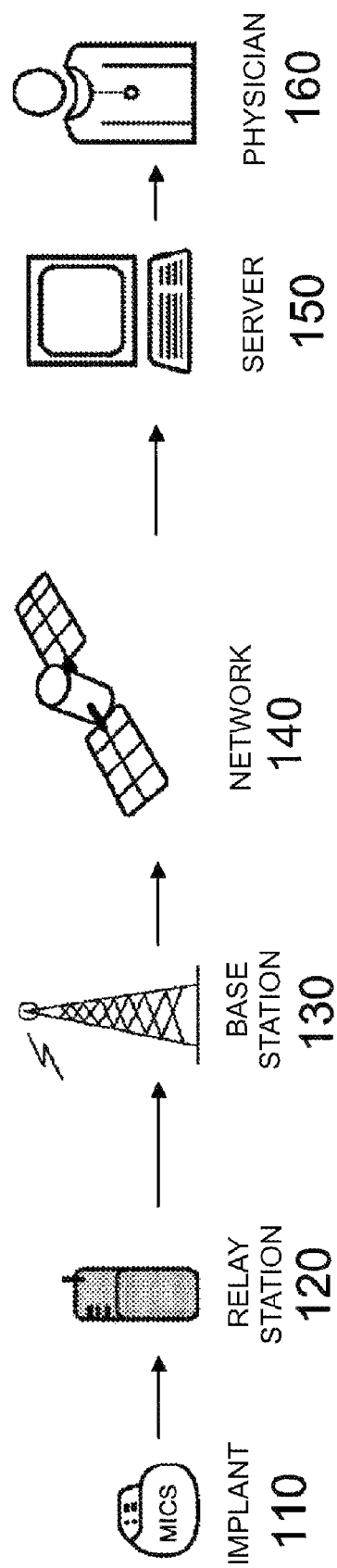
FIG. 1: shows the prior art.
Figure 2:
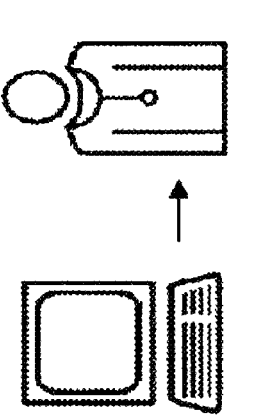
FIG. 2: shows the inventive approach as an overall system.
Figure 2:
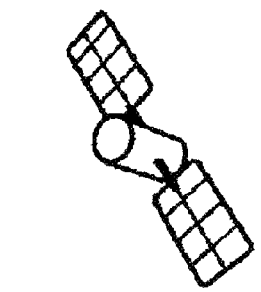
Figure 2:
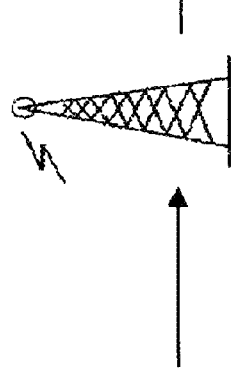
Figure 2:

FIG. 2 shows the inventive approach as part of an overall system, including an electronic implant 210 into which a GSM modem is integrated, and which always accesses a GSM base station 230 controlled by a control unit whenever the GSM band field strength makes low-current access and data transmission appear likely. The further transmission link with the mobile wireless network 240, remote monitoring server 250, and the physician 260 remains unaffected by the present invention.

Figure 3:
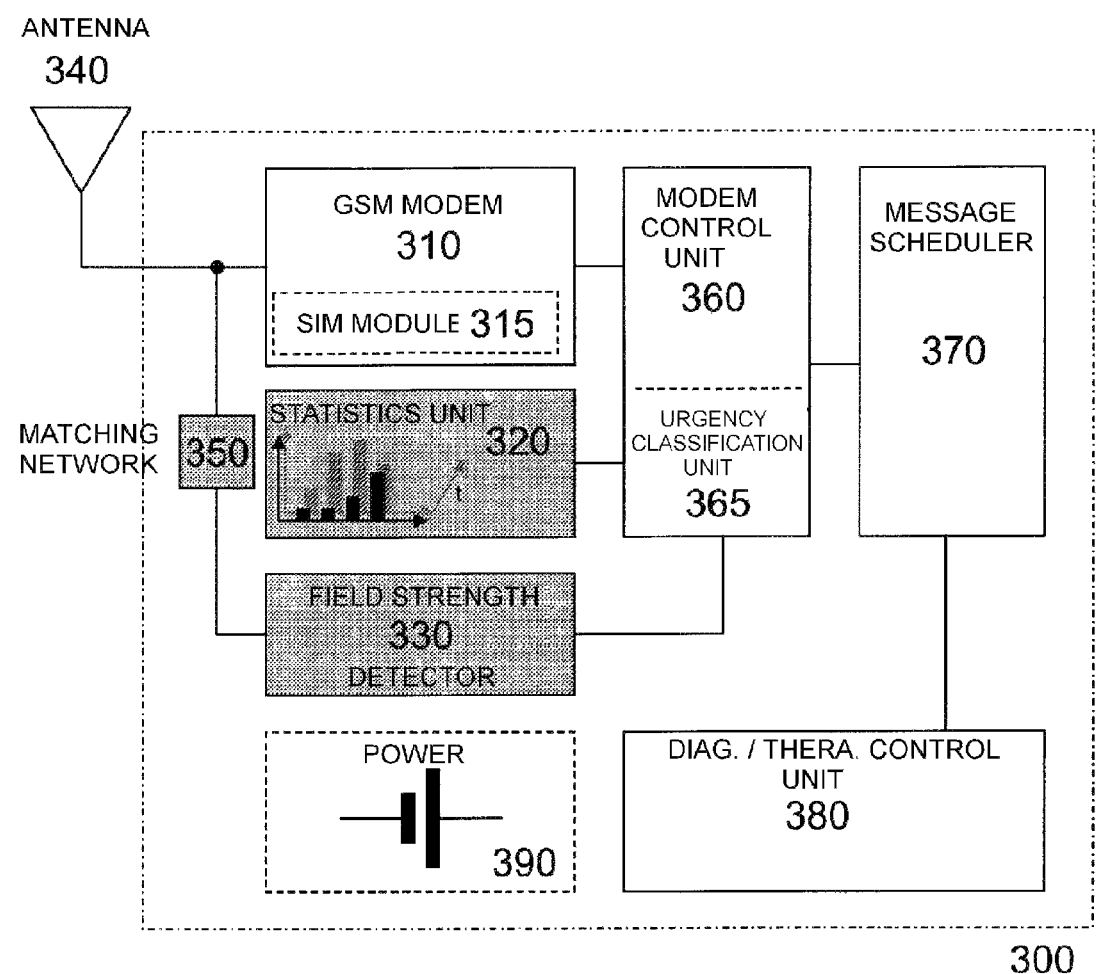
FIG. 3: shows a block diagram of an electronic implant with an integrated GSM modem.

FIG. 3 shows a block diagram of an electronic implant 210 with an integrated GSM modem. A low-current GSM modem 310 including a SIM module 315 is integrated into a hermetically sealed housing 300 of the electronic implant 210. A control unit 360 controls the GSM modem 310. The GSM modem 310 is connected to a GSM antenna 340. An extremely low-current GSM field-strength detector 330 is connected to the GSM antenna 340 via a matching network 350, and has a programmable triggering threshold. This GSM field-strength detector 330 is also connected to the control unit 360. The control unit 360 is in turn connected to a message scheduler 370.

Furthermore, the electronic implant 210 contains a diagnostic and therapeutic control unit 380. This diagnostic and therapeutic control unit 380 is connected to the message scheduler 370, so that when triggered by diagnostic or therapeutic events, the message scheduler 370 can be influenced. This may in turn be designed to request both periodic and event-triggered message transmissions. If there is such a message request, then the control unit 360 is activated. At periodic intervals, this control unit 360 then activates the field-strength detector 330 to detect a point in time when a GSM connection with a low output power can be established. If the field-strength detector 330 reports a suitable output condition (e.g., when it measures an adequate mobile wireless field strength), then the control unit 360 activates the GSM modem 310 for access to the base station 230 with the identification data of the SIM module 315. The output power of the GSM modem 310 is adapted to the signal conditions and is much lower in comparison with traditional GSM modems.

In addition, this arrangement also includes a statistics unit 320 for statistical determination of the transmission success. This statistics unit 320 always determines the transmission success rate based on the GSM field strength measured before the connection is established. This statistical determination is preferably performed as a three-dimensional histogram in which the third dimension is the time of day. It is thus possible to determine transmission conditions that recur at certain times of day (e.g., during the time the patient is in the office, etc.). As an alternative, the time determination may be expanded to a greater period, e.g., an entire week.

The control unit 360 again contains a classification unit 365 for classifying the urgency of the message. A distinction is made here, e.g., between routine messages (e.g., remote follow-up data), messages of moderate urgency (e.g., ventricular fibrillation episode with successful treatment) and emergency messages (e.g., unsuccessful maximum energy shock in the implantable cardioverter/defibrillator). Depending on the urgency determined in this classification unit 265, a different transmission success rate is assumed by the controller 360 before the connection is established.

Figure 4:
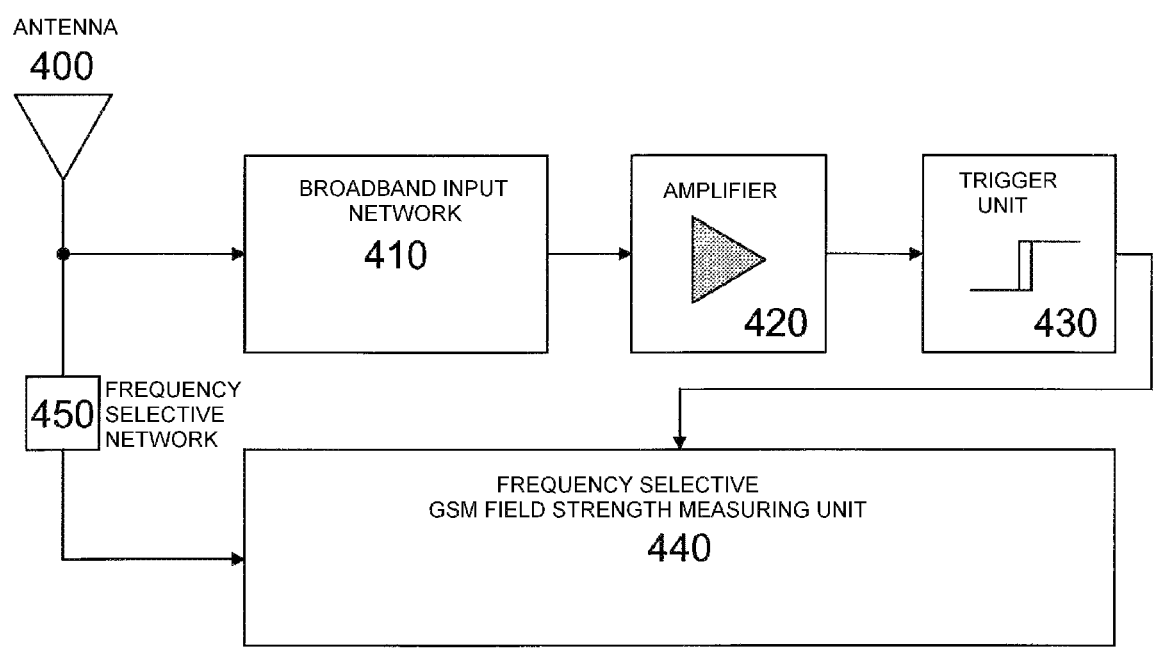
FIG. 4: shows a two-step GSM field-strength detector.

FIG. 4 shows a two-step GSM field-strength detector according to a preferred version of the invention. The goal is to implement an extremely low-current detector. For this reason, this GSM field-strength detector has a first broadband detector stage 410, 420, 430 which serves as a nonspecific GSM field-strength detector. The antenna 400 is connected to a broadband input network 410. After amplification of the GSM signal by an amplifier 420, the signal field strength is made available to a programmable trigger unit 430, which performs a threshold value comparison by means of an integrated comparator and triggers an activation signal, if necessary. The input network 410, the amplifier 420 and the trigger unit 430 form the first broadband detector stage as a nonspecific GSM field-strength detector, which activates a second specific frequency-selective GSM field-strength detector stage only when the input signal exceeds a programmable threshold for a certain period of time. The second detector stage is preferably provided as a GSM field-strength-measuring unit 440 connected by a corresponding frequency-selective network 450 to the GSM antenna.

The frequency-selective GSM field-strength-measuring unit 440 can check other specific signal characteristics in addition to the field strength, e.g., a particular signal/noise ratio, to increase the probability of a successful GSM access. If these tests are positive, then a corresponding output signal is generated.

It will be shown below that when using the inventive approach, a GSM modem can be used in an electronic implant, and this is demonstrated on the example of an implantable cardioverter/defibrillator (ICD):

(A) State of the Art

| | |
|---|---|
| Battery capacity: | ~2.3 Ah at a battery voltage of 3 V |
| Typical operating time of an ICD: | 6 years |
| Data transmission scheme for remote monitoring: | 1 access attempt per day + 5 event messages per year |
| Power demand with standard GSM access (e.g., GPRS): | |
| Access duration: | up to 10 sec |
| Power consumption at an operating voltage of 3 V: | up to 1 A |

Charge for remote monitoring = 370 access attempts × 6 years × 10 sec × 1 A = 6.1 Ah In other words, a GSM approach is impossible with the current access protocol.

(B) Exemplary Version of Invention

| | |
|---|---|
| Battery capacity: | ~2.3 Ah at an operating voltage of 3 V |
| Typical operating time of an ICD: | 6 years |
| Data transmission scheme for remote monitoring: | 1 access attempt per day + 5 event messages per year |
| Power demand with field-strength-dependent GSM access: | |
| Access duration: | up to 3 sec |
| Power consumption at an operating voltage of 3 V: | up to 0.25 A |

Charge for remote monitoring = 370 access attempts × 6 years × 3 sec × 0.25 A = 0.5 Ah With the inventive approach, GSM access by the implant is possible. With no change in the transmission schedule, the battery load is 20% of its capacity. This battery capacity required for the data transmission is on the order of magnitude of the increase in battery capacity to be expected in the coming years with the same battery volume.

(C) Exemplary Version of Invention with Reduced Data Transmission

| | |
|---|---|
| Battery capacity: | ~2.3 Ah at an operating voltage of 3 V |
| Typical operating time of an ICD: | 6 years |
| Data transmission scheme for remote monitoring: | 1.5 access attempts per week 5 event messages per year |
| Power demand with field-strength-dependent GSM access: | |
| Access time: | up to 3 sec |
| Power consumption at an operating voltage of 3 V: | up to 0.25 A |

1.5 access attempts per week means that there are max. 2 access attempts per week. If the first is successful, then the second attempt is not initiated. In the calculation, a 50% success rate of the first access attempt is assumed.
Charge for remote monitoring = 83 access attempts × 6 years × 3 sec × 0.25 A = 0.1 Ah With the invention and an adjusted data transmission protocol, use of a GSM modem in an ICD is possible without any significant restriction on the operating lifetime (<5%) of the ICD.

Figure 5:
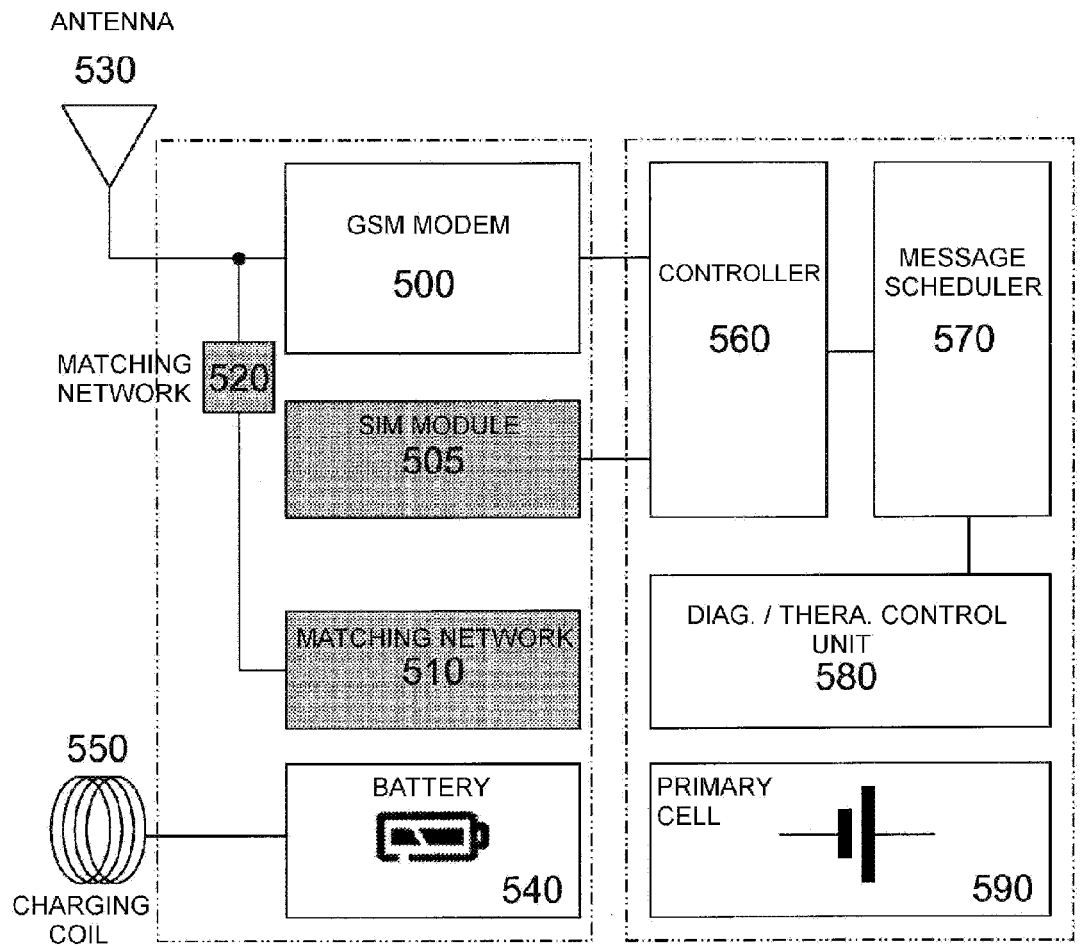
FIG. 5: shows a block diagram of an alternative implementation.

FIG. 5 shows the block diagram of an alternative implementation. In this version, the GSM modem 500 with the antenna 530, the SIM module 505 and the field-strength detector plus the matching network 510, 520 is supplied with power by its own rechargeable battery 540. The charging of this battery 540 takes place, e.g., via a charging coil 550 mounted outside of the metal implant housing.

The critical medical functions of the electronic implant, i.e., the diagnostic and therapeutic control unit 580 as well as the message scheduler 570 and controller 560 are supplied with power by a primary cell 590 as the current source or voltage source, so that the recharging of the battery that is regularly required is not a safety-relevant problem of the medical product but instead merely ensures the data transmission.

Figure 6:
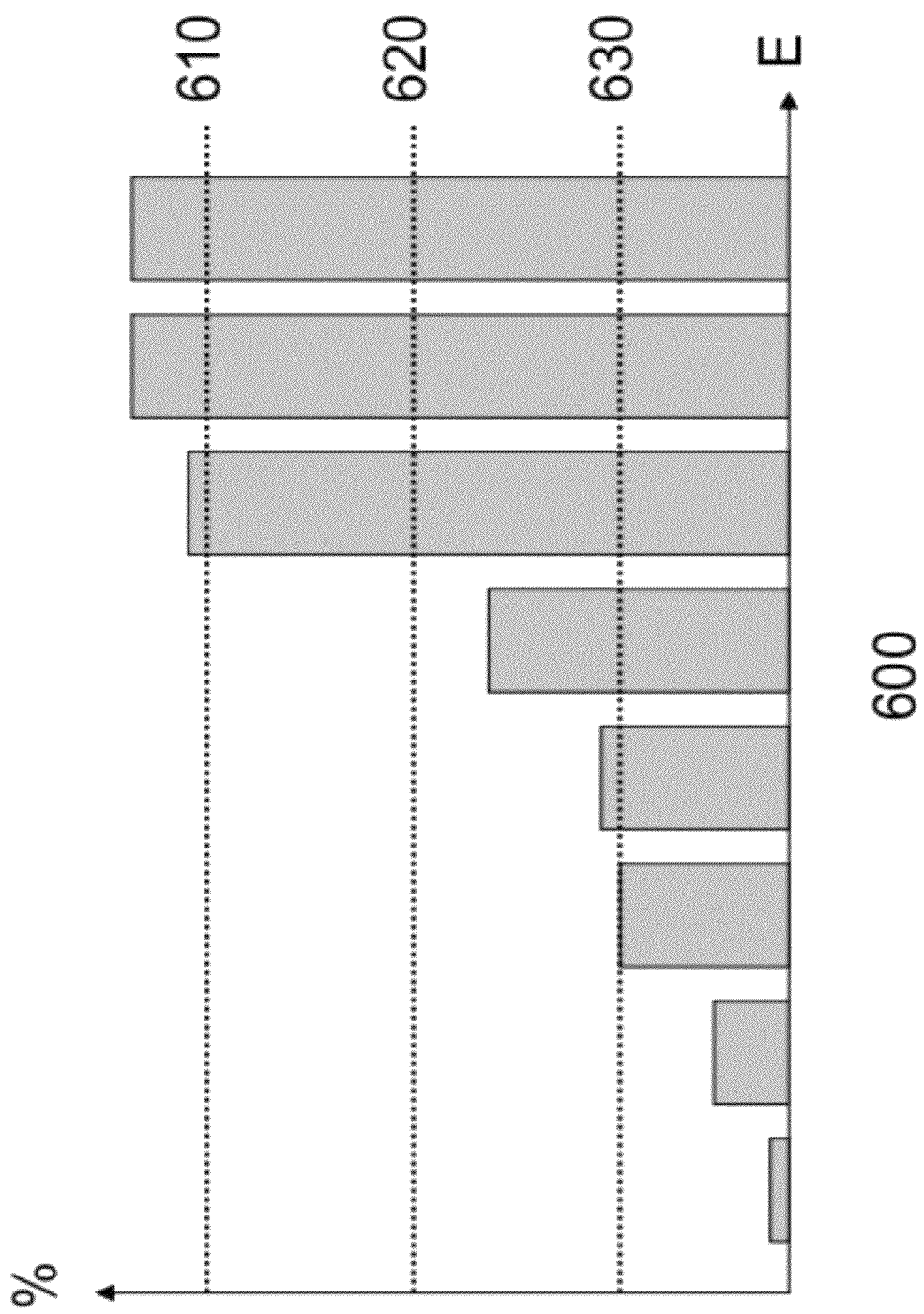
FIG. 6: shows a transmission success statistics discussed in relation to FIG. 3.

FIG. 6 shows the access success statistics mentioned in the description of FIG. 3 in the form of a histogram 600 of transmission success rates for a certain time of day.

The individual histogram classes indicate whether a data transmission has been successfully terminated, based on a field strength class measured before establishing the connection.

For the individual urgency classes of the messages, different limits (610 . . . 630) (minimum transmission success rates) are defined for the required transmission success rate. A connection is established only when the transmission success rate as indicated by the histogram exceeds the threshold programmed for the particular urgency of the message (minimum transmission success rate). Thus, in the event of an emergency message, a transmission attempt is initiated even when there is a low success rate (630), but in the event of a routine message, a transmission is initiated only when there is a very good success rate above the minimum transmission success rate, labeled as 610.

Optionally, the transmission power may be increased in the event of emergency messages in combination with a poor transmission success rate (630).

Since the invention is not limited to the use of GSM as the transmission standard, additional transmission methods, e.g., according to the mobile wireless standards UMTS, HSDPA, HSUPA or LTE, but also Bluetooth, WLAN or the like may equally be used instead of GSM.

It will be apparent to those skilled in the art that numerous modifications and variations of the described examples and versions of the invention are possible in light of the foregoing discussion. The disclosed examples and versions are presented for purposes of illustration only. Therefore, it is the intent to cover all such modifications and alternate versions as may come within the true scope of this invention.

What is claimed is:

1. An electronic implant configured to detect at least one technical or physiological patient parameter, the electronic implant including:
   a. a mobile wireless antenna;
   b. a mobile wireless modem connected to the mobile wireless antenna, the mobile wireless modem having low power consumption and low maximum transmission power;
   c. a mobile wireless field strength measuring unit connected to at least one of:
      (1) the mobile wireless antenna, and
      (2) a secondary antenna;
   d. a secondary field strength detector;
   e. a control unit connected to the mobile wireless field strength measuring unit and the mobile wireless modem, the control unit being:
      (1) configured to activate the mobile wireless field strength measuring unit when the secondary field strength detector indicates a threshold field strength, and
      (2) configured to:
         (a) trigger access by the mobile wireless modem to a mobile wireless network, and
         (b) transmit data content over the mobile wireless network, in dependence on:
            i. a field strength measured by the mobile wireless field strength measuring unit, wherein access to the mobile wireless network is triggered when the measured field strength meets or exceeds a minimum transmission success threshold, and
            ii. the urgency of the data content to be transmitted over the mobile wireless network, wherein data content of greater urgency is transmitted at or below the minimum transmission success threshold.

2. The electronic implant of claim 1 wherein the electronic implant contains a subscriber identity module (SIM).

3. The electronic implant of claim 2 wherein:
   a. the mobile wireless modem is a GSM modem, and
   b. the mobile wireless field strength measuring unit is a GSM field strength measuring unit.

4. The electronic implant of claim 1 wherein the electronic implant further includes a statistics unit which is:
   a. part of, or in communication with, the control unit; and
   b. configured to generate and record an access success statistic for access to the mobile wireless network, the access success statistic being recorded with reference to the measured field strength triggering the access to the mobile wireless network.

5. The electronic implant of claim 4 wherein the control unit is also configured to:
   a. trigger access by the mobile wireless modem to the mobile wireless network, and
   b. transmit data content over the mobile wireless network, in dependence on access success statistics recorded for several different measured field strengths, wherein access to the mobile wireless network is triggered when the current field strength measured by the mobile wireless field strength measuring unit has an access success statistic indicative of higher likelihood of successful access to the mobile wireless network.

6. The electronic implant of claim 4 wherein the statistics unit is further configured to record the access success statistic with reference to the time at which access to the mobile wireless network is triggered.

7. The electronic implant of claim 4 wherein the control unit is configured to:
   a. trigger access by the mobile wireless modem to a mobile wireless network, and
   b. transmit data content over the mobile wireless network, in dependence on:
      i. the access success statistics, and
      ii. the urgency of the data content to be transmitted over the mobile wireless network,
   with:
      (1) data content of low urgency being transmitted where the access success statistics are indicative of higher likelihood of successful access to the mobile wireless network, and
      (2) data content of high urgency being transmitted where the access success statistics are indicative of lower likelihood of successful access to the mobile wireless network.

8. The electronic implant of claim 1 wherein the electronic implant has two power sources, wherein one of the power sources is a rechargeable battery supplying power to at least the mobile wireless modem and the mobile wireless field strength measuring unit.

9. The electronic implant of claim 1 wherein the control unit is configured to
   a. operate during successive access attempt periods, and
   b. trigger access by the mobile wireless modem to the mobile wireless network no more than once during each adjustable access attempt period, each adjustable access attempt period being at least an hour in duration.

10. The electronic implant of claim 1 wherein the control unit:
    a. operates during sequential access attempt periods, each access attempt period being at least an hour in duration, and
    b. is configured to limit the number of access attempts within each access attempt period.

11. The electronic implant of claim 2 wherein the control unit is configured to always trigger access by the mobile wireless modem to the mobile wireless network in the event of data contents of greatest urgency.

12. The electronic implant of claim 1 wherein the control unit is configured to trigger access by the mobile wireless modem to the mobile wireless network only for data contents generated by a technical or physiological patient parameter detected by the electronic implant.

13. The electronic implant of claim 1 wherein the control unit is configured to trigger access by the mobile wireless modem to the mobile wireless network via an emergency number only in the event of data contents containing emergency messages.

14. An electronic implant including:
    a. a diagnostic/therapeutic unit configured to obtain patient data relating to one or more physiological patient parameters;
    b. an antenna;
    c. a mobile wireless modem in communication with the antenna;
    d. a mobile wireless field strength measuring unit;
    e. a secondary field strength detector; and
    f. a control unit configured to:

(1) activate the mobile wireless field strength measuring unit when the secondary field strength detector indicates a threshold field strength; and
(2) attempt transmission of data content over a mobile wireless network via the mobile wireless modem, wherein:
(a) the data content is dependent on the patient data, and
(b) a transmission attempt by the control unit is dependent on:
(i) a field strength measured by the mobile wireless field strength measuring unit, wherein the transmission attempt occurs when the measured field strength meets or exceeds a minimum transmission success threshold, and
(ii) an urgency rating of the data content to be transmitted over the mobile wireless network, wherein the transmission attempt occurs:
A. when data content has greater urgency, and
B. regardless of the measured field strength.

15. The electronic implant of claim 14 further including a statistics unit configured to generate and record access success statistics for prior transmission attempts by the mobile wireless modem, the access success statistics including:
a. the times of the prior transmission attempts by the mobile wireless modem;
b. the field strengths measured by the mobile wireless field strength measuring unit at the times of the prior transmission attempts; and
c. whether the prior transmission attempts successfully resulted in transmission of data content over the mobile wireless network;
wherein the transmission attempt by the control unit is dependent on whether the field strength measured by the mobile wireless field strength measuring unit corresponds to successful transmission of data content in the prior transmission attempts.

16. The electronic implant of claim 15 wherein the transmission attempt by the control unit is also dependent on whether the time of the transmission attempt corresponds to successful transmission of data content in the prior transmission attempts.

17. An electronic implant including:
a. a diagnostic/therapeutic unit configured to obtain patient data relating to one or more physiological patient parameters;
b. an antenna;
c. a mobile wireless modem in communication with the antenna;
d. a mobile wireless field strength measuring unit;
e. a secondary field strength detector;
f. a control unit configured to:
(1) activate the mobile wireless field strength measuring unit when the secondary field strength detector indicates a threshold field strength; and
(2) attempt transmission of data content over a mobile wireless network via the mobile wireless modem, the data content being dependent on the patient data;
g. a statistics unit included within, or in communication with, the control unit, the statistics unit being configured to generate and record access success statistics for prior transmission attempts by the mobile wireless modem, the access success statistics including:
(1) the times of the prior transmission attempts by the mobile wireless modem;
(2) the field strengths measured by the mobile wireless field strength measuring unit at the times of the prior transmission attempts; and
(3) whether the prior transmission attempts successfully resulted in transmission of data content over the mobile wireless network;
wherein a present transmission attempt by the control unit is dependent on whether the field strength measured by the mobile wireless field strength measuring unit corresponds to successful transmission of data content in the prior transmission attempts.

18. The electronic implant of claim 17 wherein the present transmission attempt by the control unit is also dependent on whether the current time corresponds to successful transmission of data content in the prior transmission attempts.

* * * * *